United States Patent

Steiner et al.

[11] Patent Number: 5,908,844
[45] Date of Patent: Jun. 1, 1999

[54] N-SUBSTITUTED AZABICYCLOALKANE DERIVATIVES, THEIR PREPARATION AND USE

[75] Inventors: Gerd Steiner, Kirchheim; Rainer Munschauer, Neustadt; Liliane Unger, Ludwigshafen; Hans-Jürgen Teschendorf, Dudenhofen; Thomas Höger, Edingen-Neckarhausen, all of Germany

[73] Assignee: BASF Aktiengesellschaft, Ludwigshafen, Germany

[21] Appl. No.: 08/640,751

[22] PCT Filed: Oct. 31, 1994

[86] PCT No.: PCT/EP94/03583

§ 371 Date: May 6, 1996

§ 102(e) Date: May 6, 1996

[87] PCT Pub. No.: WO95/13279

PCT Pub. Date: May 18, 1995

[30] Foreign Application Priority Data

Nov. 10, 1993 [DE] Germany ............... 43 38 396

[51] Int. Cl.⁶ .................... A61K 31/505; C07D 403/04; C07D 403/06
[52] U.S. Cl. .................... 514/258; 514/259; 514/272; 514/275; 544/253; 544/278; 544/282; 544/284; 544/285; 544/286; 544/287; 544/320; 544/321; 544/330; 544/331

[58] Field of Search .................... 544/285, 286, 544/287, 253, 278, 282, 284, 320, 321, 330, 331; 514/259, 258, 272, 275

[56] References Cited

U.S. PATENT DOCUMENTS 3,960,861  6/1976  Danilewicz et al. ............ 544/284
5,049,564  9/1991  DeBernardis et al. .......... 514/290

FOREIGN PATENT DOCUMENTS 70 053     1/1983   European Pat. Off. .
196 132   10/1986   European Pat. Off. .
WO93/16050  8/1983   WIPO .
WO94/00458  1/1994   WIPO .

Primary Examiner—Richard L. Raymond
Attorney, Agent, or Firm—Keil & Weinkauf

[57] ABSTRACT

Compounds of the formula I

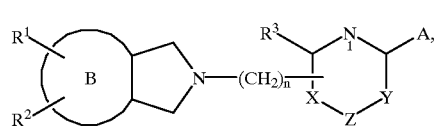

where B, $R^1$, $R^2$, n, $R^3$, A, X, Y and Z have the meanings stated in the description, and their preparation are described. The novel ompounds are suitable for controlling diseases.

9 Claims, No Drawings

N-SUBSTITUTED AZABICYCLOALKANE DERIVATIVES, THEIR PREPARATION AND USE

This is a 371 application of PCT/EP94/03583, filed Oct. 31, 1994.

The present invention relates to novel N-substituted azabicycloalkane derivatives, their preparation and use for preparing pharmaceutical active substances.

It is known that 5- or 6-membered heterocyclic nitrogen derivatives with basic substituents have neuroleptic effects (EP 196 132, EP 70 053, DE 42 43 287).

In this context the observed high affinities for serotonin receptors appear, besides the dopamine receptor subtype affinities, to be particularly important.

We have now found that N-substituted 3-azabicycloalkane derivatives of the formula I

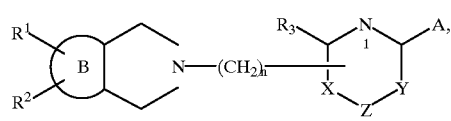

where
B is a 3-, 5- or 6-membered ring which, in addition to carbon atoms, may contain 1 nitrogen atom and/or 1 oxygen atom and optionally a double bond, $R^1$ is phenyl which is unsubstituted or mono- or disubstituted by halogen atoms, $C_1-C_4$-alkyl, trifluoromethyl, hydroxyl, $C_1-C_4$-alkoxy, amino, monomethylamino, dimethylamino, cyano or nitro groups, $R^2$ is hydrogen, a $C_1-C_4$-alkyl, or phenyl which is unsubstituted or substituted by halogen, methoxy, hydroxyl or amino, n is 0, 1, 2, 3 or 4, $R^3$ is hydrogen, hydroxyl, $C_1-C_4$-alkyl or $C_1-C_4$-alkoxy or, together with the adjacent carbon atom, a C=O or C=S group, X and Y are carbon atoms, CH, $CH_2$, NH or $C_1-C_4$-alkyl-N groups or nitrogen atoms, Z is a direct linkage, a CO group, CS group or a CH or $CH_2$ group in which one hydrogen atom can be replaced by a hydroxyl, amino or $C_1-C_4$-alkoxy group or a halogen atom, and A is hydrogen, hydroxyl, amino, mercapto, $C_1-C_4$-alkylamino, di-$C_1-C_4$-alkylamino, $C_1-C_4$-alkylthio or $C_1-C_4$-alkoxy or, together with the adjacent carbon atom, a C=O group, or A is a $C_3-C_4$-alkylene group which is linked to Y and which may contain one or two non-cumulative double bonds and in which one CH or $CH_2$ group may be replaced by a nitrogen or sulfur atom or an NH or N—$CH_3$ group and where the ring may be monosubstituted either by a fluorine or chlorine atom or a methyl, methoxy, nitro or amino group or, in the case of a benzene ring, the latter may be mono-, di- or trisubstituted by fluorine or chlorine atoms or methyl, trifluoromethyl, nitro, hydroxyl, methoxy, amino, monomethyl- or dimethylamino groups, and where the ring on the right of the formula I may have on nitrogen atom No. 1 hydrogen atom or a $C_1-C_4$-alkyl group and may contain 1–3 non-cumulative double bonds, and salts thereof with physiologically tolerated acids, have valuable pharmacological properties.

The following meanings of the substituents $R^1$, $R^2$, $R^3$ and n should be particularly mentioned:

$R^1$: phenyl, unsubstituted or substituted by fluorine, chlorine, methoxy, nitro, trifluoromethyl, hydroxyl or amino, $R^2$: hydrogen, methyl, $R^3$: methyl, hydroxyl, n: 2.

The bicyclic ring system on the left of formula I is, in particular,

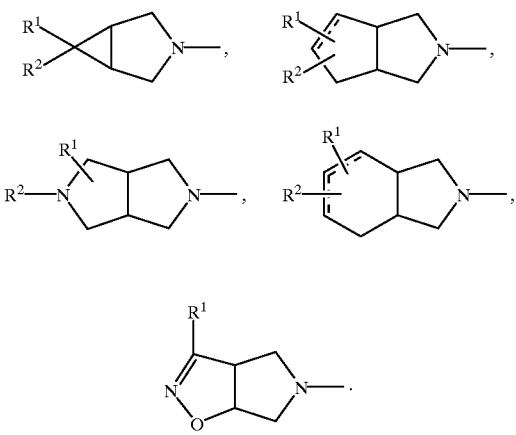

The ring system on the right in formula I is, in particular,

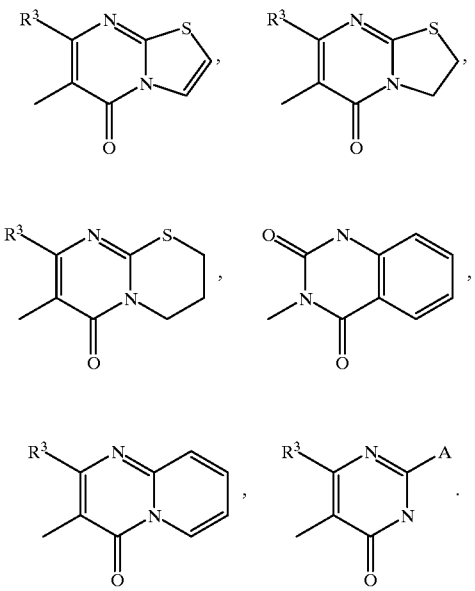

Particularly preferred compounds are those where $R^1$ is preferably phenyl which is substituted in the p position by fluorine and chlorine or in the m position by fluorine or chlorine $R^2$ is hydrogen or methyl and $R^3$ is methyl or hydroxyl and the ring system on the right of the molecule is derived from 7-methyl-5H-thiazolo[3,2-a]pyrimidin-5-one,
2(3H)-benzimidazolone,
2-indolinone, 2,4(1H,3H)-quinazolinedione,
2(1H)-quinolone,
2-methyl-4H-pyrido[1,2-a]pyrimidin-4-one or
2-methylamino-3,6-dimethyl-4(3H)-pyrimidinone.

The compounds of the formula I according to the invention can be prepared by reacting a compound of the formula II

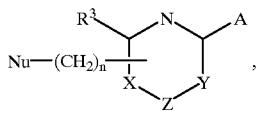

where n, $R^3$, X, Y, Z and A have the abovementioned meanings, and Nu is a nucleofugic leaving group, with a 3-azabicycloalkane derivative of the formula III

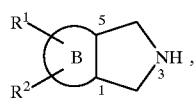

where B, $R^1$ and $R^2$ have the abovementioned meanings, and converting the resulting compound where appropriate into the addition salt with a physiologically tolerated acid.

Suitable and preferred nucleofugic leaving groups Nu are halogen atoms, especially bromine or chlorine.

The reaction is expediently carried out in the presence of an inert base such as triethylamine or potassium carbonate as acid trap in an inert solvent such as a cyclic saturated ether, especially tetrahydrofuran or dioxane, or an aromatic hydrocarbon such as toluene or xylene.

The reaction is, as a rule, carried out at from 20 to 150° C., in particular from 80 to 140° C., and is generally complete within 1–10 hours.

The compounds of the formula I according to the invention can either be recrystallized by recrystallization from conventional organic solvents, preferably from a lower alcohol, such as ethanol, or be purified by column chromatography.

Racemates can be fractionated into the enantiomers in a simple way by classical resolution using optically active carboxylic acids, e.g. tartaric acid derivatives, in an inert solvent, e.g. lower alcohols.

The free 3-azabicycloalkane derivatives of the formula I can be converted in a conventional way into the addition salt of a pharmacologically suitable acid, preferably by mixing a solution with one equivalent of the appropriate acid. Examples of pharmaceutically suitable acids are hydrochloric acid, phosphoric acid, sulfuric acid, methanesulfonic acid, sulfamic acid, maleic acid, fumaric acid, oxalic acid, tartaric acid and citric acid.

The compounds according to the invention have valuable pharmacological properties. They can be used as neuroleptics (especially atypical), antidepressants, sedatives, hypnotics, CNS protectives or muscle relaxants. It is possible for a plurality of the said types of action to occur in combination in one compound according to the invention. The pharmacological effect is demonstrated both in vivo and in vitro, and it is possible to characterize the substances in particular by the affinity, which is very high and selective in some cases, for receptor subtypes, e.g. dopamine $D_1$, $D_2$, $D_3$ and, in particular, $D_4$ receptors; serotonin 1A, 1D and 2 receptors, alpha 1 and 2 receptors; histamine 1 and muscarine receptors.

The following methods were used for the in vivo characterization:

a) Effect on orientation motility

In a new environment, mice show an exploratory behavior which is manifested by increased motor activity. This motor activity is measured in light barrier cages for 0–30 min after the animals (female NMRI mice) have been placed in the cages. ED50: dose which reduces the motor activity by 50% compared with placebo-treated controls.

b) Apomorphine antagonism

Female NMRI mice receive 1.21 mg/kg apomorphine s.c. At this dose, apomorphine leads to motor activation which is manifested when the animals are kept in wire mesh cages by continuous climbing. The climbing is evaluated by a score every 2 min for 30 min:

0: animal has four paws on the floor

1: animal has two paws on the wire

2: animal has four paws on the wire (is climbing).

The climbing behavior can be inhibited by pretreatment with antipsychotics.

ED50: dose which inhibits the climbing activity of the animals by 50% compared with placebo-treated controls.

c) Methamphetamine antagonism

Female NMRI mice receive 1 mg/kg methamphetamine orally and, after 30 min, are placed in light barrier cages to measure the motor activity (2 animals/cage, 4 cages/dose). The test substances are administered orally 30 min before methamphetamine. The increase in activity due to methamphetamine is calculated for the period 15–60 min after the animals have been placed in the cage as the difference between the methamphetamine controls and the placebo controls and set equal to 100%. The ED100 is the dose of test substance which completely abolishes the increase in activity.

d) L-5-HTP antagonism

Female Sprague-Dawley rats receive L-5-HTP in a dose of 316 mg/kg i.p. The animals subsequently develop an excitation syndrome of which the symptoms for paw treading and tremor are evaluated with a score (0=absent, 1=moderate, 2=pronounced) every 10 min in the period from 20 to 60 min after L-5-HTP administration. The average score after L-5-HTP administration is 17. The test substances are administered orally 60 min before L-5-HTP. The ED50 is the dose which reduces the control score by 50% on average.

The above methods are suitable for characterizing substances as antipsychotics; in particular, the inhibition of the methamphetamine-induced motor stimulation is regarded as predictive of an antipsychotic effect. The inhibition of the L-5-HTP syndrome may indicate a serotonin-antagonistic effect which is a type of effect which is characteristic of atypical neuroleptic agents.

The novel compounds show a good effect in these tests.

The invention accordingly also relates to a therapeutic composition which contains a compound of the formula I or its pharmacologically suitable acid addition salt as active substance in addition to the conventional excipients and diluents, and to the use of the novel compounds for controlling diseases.

The compounds according to the invention can be administered in a conventional way orally or parenterally, intravenously or intramuscularly.

The dosage depends on the age, condition and weight of the patient and on the mode of administration. As a rule, the daily dose of active substance is about 1–100 mg/kg of body weight on oral administration and 0.1–10 mg/kg of body weight on parenteral administration.

The novel compounds can be used in conventional solid or liquid pharmacological forms, e.g. as uncoated or (film-) coated tablets, capsules, powders, granules, suppositories, solutions, ointments, creams or sprays. These are produced in a conventional way. The active substances can for this purpose be processed with the conventional pharmaceutical aids such as tablet binders, fillers, preservatives, tablet disintegrants, flow regulators, plasticizers, wetting agents, dispersants, emulsifiers, solvents, release-slowing agents, antioxidants and/or propellant gases (cf. H. Sucker et al.: Pharmazeutische Technologie, Thieme-Verlag, Stuttgart, 1978). The forms obtained in this way normally contain 1–99% by weight of the active substance.

The substances of the formula II and III required as starting materials for synthesizing the novel compounds are known or can be synthesized by preparation methods described in the literature from analogous starting materials.

The following examples serve to illustrate the invention:

Preparation of the Precursors

A. Exo-2-phenyl-3-methyl-1,5-cis-3,7-diazabicyclo[3.3.0]octane a) 6-Phenyl-7-methyl-1,5-cis-3,7-diazabicyclo[3.3.0]-octane-2,4-dione 17.8 g (200 mM) of sarcosine, 15.2 ml (150 mmol) of benzaldehyde and 9.7 g (100 mM) of maleimide were suspended in 500 ml of toluene and refluxed in a Dean and Stark apparatus for 3 h. Then a further 17.8 g (200 mM) of sarcosine and 15.2 ml (150 mM) of benzaldehyde were added, and the mixture was refluxed for a further hour. After cooling, 50 g of sodium sulfate were added and, after stirring for a few minutes, filtered off. The filtrate was concentrated, and the remaining viscous oil (37.2 g) was purified by column chromatography (silica gel, mobile phase dichloromethane/methanol 98/5). This resulted in 4.2 g (18%) of enriched endo adduct (endo:exo=80:20) and 10.7 g (47%) of enriched exo adduct (exo:endo=80:20).

b) Exo-2-phenyl-3-methyl-1,5-cis-3,7-diazabicyclo[3.3.0]octane

A solution of 8.5 g (37 mM) of enriched exo-6-phenyl-7-methyl-1,5-cis-3,7-diazabicyclo[3.3.0]octane-2,4-dione in 130 ml of absolute tetrahydrofuran was added dropwise to a suspension of 7.0 g (185 mM) of lithium aluminum hydride in 180 ml of absolute tetrahydrofuran at room temperature over the course of 25 min with vigorous stirring. After the slightly exothermic reaction had subsided, the mixture was stirred at room temperature for 18 h. Then, while cooling in ice, 70 ml of ten percent sodium hydroxide solution was slowly added dropwise with vigorous stirring, and the mixture was allowed to reach room temperature with stirring. The precipitated hydroxides were filtered off with suction and washed several times with tetrahydrofuran, and the combined filtrates were concentrated. 6.3 g (84%) of pale oil were isolated.

B. endo-2-Phenyl-3-methyl-1,5-cis-3,7-diazabicyclo[3.3.0]octane

As in method A.b), 3.0 g (81%) of cloudy oil were obtained from 4.2 g (18 mM) of enriched endo-6-phenyl-7-methyl-1,5-cis-3,7-diazabicyclo[3.3.0]octane-2,4-dione and 3.5 g (91 mM) of lithium aluminum hydride.

C. 3-Phenyl-1,5-cis-3,7-diazabicyclo[3.3.0]octane a) 7-Benzyl-3-phenyl-1,5-cis-3,7-diazabicyclo[3.3.0]octane-2,4-dione 20.1 g (100 mM) of N-benzylglycine hydrochloride, 7.5 g (250 mM) of paraformaldehyde and 8.7 g (50 mM) of N-phenylmaleimide were suspended in 500 ml of toluene, and finally 17.4 ml (100 mM) of N-ethyldiisopropylamine were added. The mixture was refluxed for 30 min in a Dean and Stark apparatus and then filtered through sodium sulfate, and the filtrate was concentrated. The remaining viscous oil (18.6 g) was purified by column chromatography (silica gel, mobile phase dichloromethane). 8.7 g (56%) of pale oil were obtained.

b) 7-Benzyl-3-phenyl-1,5-cis-3,7-diazabicyclo[3.3.0]octane

A solution of 8.7 g (28 mM) of 7-benzyl-3-phenyl-1,5-cis-3,7-diazabicyclo[3.3.0]octane-2,4-dione in 100 ml of absolute tetrahydrofuran was slowly added dropwise to a suspension of 2.65 g (71 mM) of lithium aluminum hydride in 75 ml of absolute tetrahydrofuran at room temperature. The mixture was then refluxed for 2 h. Subsequently, while cooling in ice, 30 ml of ten percent sodium hydroxide solution were slowly added dropwise, and the precipitated hydroxides were filtered off with suction. Washing with tetrahydrofuran and concentration of the combined filtrates afforded 7.2 g of a cloudy oil, which was purified by column chromatography (silica gel, dichloromethane/methanol 97:3). Yield: 5.8 g (73%) of clear oil.

c) 3-Phenyl-1,5-cis-3,7-diazabicyclo[3.3.0]octane 5.8 g (21 mM) of 7-benzyl-3-phenyl-1,5-cis-3,7-diazabicyclo[3.3.0]octane were dissolved in 170 ml of methanol, and 0.7 g of palladium on carbon (10%) was added. Then, while stirring, a solution of 6.6 g (104 mM) of ammonium formate in 7 ml of water was added dropwise. The mixture was then stirred at 50° C. for 3 h and subsequently a further 0.5 g of palladium on carbon (10%) was added, and the mixture was stirred at 50° C. for a further hour. The catalyst was filtered off with suction and thoroughly washed with methanol, and the combined filtrates were evaporated to dryness. The residue was taken up in water, adjusted to pH 9–10 and extracted three times with dichloromethane. Drying and concentration of the organic phase provided 3.0 g of white solid, which was digested in a little ether. Filtration with suction and drying yielded 1.7 g (43%) of fine colorless crystals.

D. exo-6-Phenyl-3-azabicyclo[3.1.0]hexane a) cis-1,2-Bis(hydroxymethyl)-trans-3-phenylcyclopropane A solution of 20.0 g (85 mM) of dimethyl trans-3-phenyl-cis-1,2-cyclopropanedicarboxylate in 250 ml of absolute tetrahydrofuran was slowly added dropwise to a suspension of 7.9 g (213 mM) of lithium aluminum hydride in 150 ml of absolute tetrahydrofuran while cooling in ice at 0° C. The mixture was allowed slowly to reach room temperature and was then stirred for 18 h. Subsequently, while cooling in ice, 70 ml of ten percent sodium hydroxide solution were slowly added dropwise, and the precipitated hydroxides were filtered off with suction and washed with tetrahydrofuran. Concentration of the filtrate yielded 14.7 g (97%) of viscous yellow oil.

b) cis-1,2-Bis(methanesulfonyloxymethyl)-trans-3-phenylcyclopropane

A solution of 14.7 g (82 mM) of cis-1,2-bis(hydroxymethyl)-trans-3-phenylcyclopropane in 70 ml absolute pyridine was added dropwise to a solution of 32.2 g (281 mM) in 350 ml of absolute pyridine at −5° C. at such a rate that the internal temperature did not exceed 0° C., and the mixture was then stirred at −5° C. for 3 h. The cold mixture was subsequently poured onto ice-water to which 60 ml of concentrated sulfuric acid had been added. The mixture was then stirred for 1 h, and the supernatant solution was decanted off from the oily precipitate, the latter was taken up in a little dimethylformamide, and this solution was poured onto ice-water with stirring. After stirring for 1 h, the microcrystalline precipitate was filtered off with suction, washed with water and dried. 19.6 g (78%) of pale powder were obtained.

c) 3-(4-Methoxyphenylmethyl)-exo-6-phenyl-3-azabicyclo [3.1.0]hexane 5.0 g (16.6 mM) of cis-1,2-bis(methanesulfonyloxymethyl)-trans-3-phenylcyclopropane were added to 6.8 g (50 mM) of 4-methoxybenzylamine, and the mixture was heated at 100° C. with vigorous stirring for 2 h. After cooling, the mixture was dissolved in methylene chloride, and the organic phase was washed twice with water and, after drying with sodium sulfate, concentrated. The crude product (4.9 g) was purified by column chromatography (silica gel, mobile phase methylene chloride/methanol 99/1). 2.2 g (48%) of product were isolated as a yellow oil.

d) exo-6-Phenyl-3-azabicyclo[3.1.0]hexane 2.2 g (7.9 mM) of 3-(4-methoxyphenylmethyl)-exo-6-phenyl-3-azabicyclo[3.1.0]hexane were dissolved in 70 ml of methanol, and 0.6 g of palladium on carbon (10%) was added. Then, while stirring, a solution of 2.5 g (39 mM) of ammonium formate in 3 ml of water was added dropwise. The mixture was then stirred at 50° C. for 1 h. The catalyst was filtered off with suction and thoroughly washed with methanol, and the combined filtrates were evaporated to dryness. The residue was taken up in water, adjusted to pH 9–10 and extracted three times with dichloromethane. Drying and cautious concentration of the organic phase at a maximum bath temperature of 30° C. afforded 1.1 g (88%) of product as a yellow oil.

E. 6-(4-Fluorophenyl)-1,5-cis-3-azabicyclo[3.3.0]oct-6-ene a) 3-Benzyl-6-(4-fluorophenyl)-6-hydroxy-1,5-cis-3-azabicyclo[3.3.0]octane Under nitrogen, 1.4 g (56 mM) of magnesium turnings were added to 20 ml of absolute tetrahydrofuran, and then a solution of 9.4 g (54 mM) of 4-bromo-1-fluorobenzene in 55 ml of absolute tetrahydrofuran was added dropwise. After the slightly exothermic reaction had subsided, the mixture was stirred for 1 h. Then a solution of 10.5 g (49 mM) of 3-benzyl-6-oxo-1,5-cis-3-azabicyclo[3.3.0]-octane (K. Miyajima, M. Takemoto and K. Achiwa, Chem. Pharm. Bull. 39 (1991) 3175) in 40 ml of absolute tetrahydrofuran was added dropwise, and the mixture was consequently refluxed for 5 h. Then, while cooling in ice, 50 ml of a saturated ammonium chloride solution were added dropwise, and the precipitated hydroxides were filtered off with suction and washed with tetrahydrofuran. The combined filtrates were concentrated, the residue was taken up with water, the pH was adjusted to 11 with ten percent sodium hydroxide solution, and two extractions with dichloromethane were carried out. The organic phase was washed once with saturated sodium chloride solution, dried over sodium sulfate and concentrated. The remaining oil (14.8 g) was purified by column chromatography (silica gel, mobile phase dichloromethane/methanol 98.5/1.5). 11.5 g (75%) of yellow oil were obtained.

b) 6-(4-Fluorophenyl)-6-hydroxy-1,5-cis-3-azabicyclo [3.2.0]octane 9.0 g (29 mM) of 3-benzyl-6-(4-fluorophenyl)-6-hydroxy-1,5-cis-3-azabicyclo[3.3.0]octane were dissolved in 250 ml of methanol and 2.0 g of palladium on charcoal (10%) were added. Then, while stirring, a solution of 9.1 g (145 mM) of ammonium formate in 11 ml of water was added dropwise and, after the addition was complete, the mixture was refluxed for 3 h. The catalyst was filtered off with suction and thoroughly washed with methanol, and the combined filtrates were evaporated to dryness. The residue was taken up in water, adjusted to pH 9–10 with ten percent sodium hydroxide solution and extracted twice with dichloromethane. Drying and concentration of the organic phase yielded 5.4 g (84%) of yellowish oil.

c) 6-(4-Fluorophenyl)-1,5-cis-3-azabicyclo[3.3.0]oct-6-ene 6.9 g (31 mM) of 6-(4-fluorophenyl)-6-hydroxy-1,5-cis-3-azabicyclo[3.3.0]octane were taken up in 50 ml of half-concentrated for hydrochloric acid and refluxed for 5 h. Then, while cooling in ice, the mixture was diluted with water, the pH was adjusted to 11 with concentrated sodium hydroxide solution, and two extractions with dichloromethane were carried out. Drying and concentration of the organic phase yielded a dark oil (5.9 g), which was purified by column chromatography (silica gel, mobile phase methanol/aqueous ammonia solution 95/5). 5.3 g (84%) of brown oil were obtained.

F. 6-(4-Fluorophenyl)-1,5-cis-3-azabicyclo[3.3.0]octane 5.3 g (26.1 mM) of 6-(4-fluorophenyl)-1,5-cis-3-azabicyclo[3.3.0]oct-6-ene were dissolved in 100 ml of methanol, and 1.0 g of palladium on carbon (10%) was added. The reaction mixture was catalytically hydrogenated under atmospheric conditions. The catalyst was filtered off with suction and thoroughly washed with methanol, and the combined filtrates were evaporated to dryness. 4.4 g (82%) of product were isolated as mixture of endo and exo diastereomers, which was fractionated by column chromatography (silica gel, mobile phase methanol/ammonium hydroxide 90/10).

G. exo-7-Phenyl-1,5-cis-3-azabicyclo[3.3.0]octane

A mixture of 9.9 g (50 mM) of 3-benzyl-1,5-cis-3-azabicyclo[3.3.0]oct-6-ene (K. Miyajima, M. Takemoto and K. Achiwa, Chem. Pharm. Bull. 39 (1991) 3175), 14.0 ml (125 mM) of iodobenzene, 0.9 g (4.0 mM) of palladium(II) acetate, 2.1 g (8.0 mM) of triphenylphosphine, 4.3 g (50 mM) of piperidine and 2.3 g (50 mM) of formic acid in 100 ml of dimethylformamide was heated at 80° C. with vigorous stirring for 6 h. After the mixture had been concentrated under oil pump vacuum, the residue was partitioned between water and methylene chloride, the mixture was acidified with ten percent hydrochloric acid, and the organic phase was dried with sodium sulfate and then concentrated. The crude product was purified by column chromatography (silica gel, mobile phase ethyl acetate/n-hexane 1/1). 3.6 g (26%) of the N-benzyl derivative were isolated and converted by catalytic hydrogenation as in Example F into the final product (yellow oil).

The following can be prepared in a similar way (see Example O):

exo-7-(p-fluorophenyl)-1,5-cis-3-azabicyclo[3.3.0]octane

H. endo-6-p-Fluorophenyl-1,5-cis-3-azabicyclo[4.3.0] nonane[sic]

a) endo-3-p-Fluorophenyl-4-cyclohexene-cis-1,2-dicarboxylic anhydride 53.0 g (358 mM) of trans-1-(p-fluorophenyl)-1,3-butadiene and 34.3 g (350 mM) of maleic anhydride in 100 ml of toluene were slowly heated to 100° C. with vigorous stirring and kept at this temperature for 1.5 h. After cooling, the mixture was concentrated to half the volume and the product was allowed to crystallize while cooling in an ice bath. The crystals were filtered off with suction and washed with a little cold toluene. 59 g (69%) of product were isolated with melting point 88–90° C.

b) cis-3-p-fluorophenyl-cis-1,2-bis(hydroxymethyl)-4-cyclohexene

A solution of 12.0 g (49 mM) of endo-3-p-fluorophenyl-4-cyclohexene-cis-1,2-dicarboxylic anhydride in 60 ml of tetrahydrofuran was added dropwise to 3.5 g (92 mM) of lithium aluminum hydride in 170 ml of absolute tetrahydrofuran at room temperature while stirring vigorously over the course of 45 min. The mixture was stirred for 1.5 h and then refluxed for 2 h. After cooling, ten percent sodium hydroxide solution was cautiously added dropwise while cooling in ice and stirring vigorously, and the precipitated hydroxides were filtered off with suction. The filtrate was evaporated to dryness, and the residue was partitioned between ten percent sodium hydroxide solution and methyl-t-butyl ether. The aqueous phase was then extracted twice with methyl-t-butyl ether, and the organic phase was dried with sodium sulfate and then concentrated. 8.9 g (77%) of product were isolated as a clear oil.

c) cis-3-p-Fluorophenyl-cis-1,2-bis(methanesulfonyloxmethyl)-4-cyclohexene 19.7 g (84 mM) of cis-3-p-fluorophenyl-cis-1,2-bis (hydroxymethyl)-4-cyclohexene in 70 ml of pyridine were added dropwise at 0° C. with vigorous stirring to a solution of 28.6 g (250 mM) of methanesulfonyl chloride in 100 ml of pyridine, and the mixture was stirred at 0° C. for 2 h. It was subsequently poured onto ice-water to which 64 ml of concentrated sulfuric acid had been added, and the mixture was extracted twice with methylene chloride. The organic phases were washed twice with ten percent sulfuric acid and, after drying with sodium sulfate, concentrated. 30.3 g (92%) of product were isolated as a pale oil.

d) 3-Benzyl-endo-6-p-fluorophenyl-1,5-cis-3-azabicyclo [4.3.0]non-7-ene 21.8 g (56 mM) of cis-3-p-fluorophenyl-cis-1,2-bis (methanesulfonyloxymethyl)-4-cyclohexene were added in portions to 20 ml (183 mM) of benzylamine with vigorous stirring (exothermic reaction). The mixture was then heated at 130° C. for 2 h. After cooling, 200 ml of methyl t-butyl ether were added to the mixture, which was then stirred to allow crystallization. The crystals were filtered off with suction and washed with methyl t-butyl ether and then the filtrate was washed twice with aqueous ammonia solution, and the organic phase was dried with sodium sulfate and then concentrated. The crude product (16.5 g) was purified by column chromatography (silica gel, mobile phase ethyl acetate/n-hexane 6/4). 10.5 g (61%) of product were isolated as a pale oil.

e) endo-6-p-Fluorophenyl-1,5-cis-3-azabicyclo[4.3.0] nonane 10.0 g (32 mM) of 3-benzyl-endo-6-p-fluorophenyl-1,5-cis-3-azabicyclo[4.3.0]non-7-ene in 200 ml of methanol were catalytically hydrogenated in the presence of 1.3 g of palladium on carbon (10%) at room temperature. The catalyst was filtered off with suction and washed with methanol, and then, after concentration, 7.8 g of crude product were isolated as a pale oil which was purified by column chromatography (silica gel, mobile phase methanol/aqueous ammonia solution 85/15). 4.6 g (66%) of product were isolated with melting point 76–78° C.

The following can be prepared in a similar way:
f) endo-6-phenyl-1,5-cis-3-azabicyclo[4.3.0]nonane
g) endo-6-(p-trifluoromethylphenyl)-1,5-cis-3-azabicyclo [4.3.0]nonane
I. endo-6-p-Fluorophenyl-1,5-cis-3-azabicyclo[4.3.0]non-7-ene 20 ml of ammonia were injected into a 0.3 l stirred autoclave containing 7.6 g (19.4 mM) of cis-3-p-fluorophenyl-cis-1,2-bis(methanesulfonyloxymethyl)-4-cyclohexene in 100 ml of toluene, and the mixture was heated at 150° C. under autogenous pressure for 5 h. The mixture was then poured into ice-water, and the organic phase was filtered with suction to remove insolubles and then washed with water. After drying and concentration, 4.4 g of crude product were isolated and were purified by column chromatography (silica gel, mobile phase methanol/ aqueous ammonia solution 85/15). 0.9 g (21%) of product as colorless oil.

K. 6-p-Fluorophenyl-1,5-cis-3-azabicyclo[4.3.0]non-6-ene
a) endo-3-p-Fluorophenyl-4-cyclohexene-cis-1,2-dicarboximide 50.0 g (338 mM) of trans-1-p-fluorophenyl-1,3-butadiene and 32.0 g (330 mM) of maleimide in 100 ml of toluene were slowly heated to 100° C. with vigorous stirring and kept at this temperature for 2 h. After cooling, the mixture was concentrated to half the volume and left in an ice bath for the product to crystallize out. The crystals were filtered off with suction and washed with a little cold toluene. 69.7 g (86%) of product were isolated with melting point 184–186° C.

b) 3-p-Fluorophenyl-3-cyclohexene-cis-1,2-dicarboximide 2.4 g (80 mM) of sodium hydride (80%) were added in portions to 9.8 g (40 mM) of endo-3-p-fluorophenyl-4-cyclohexene-cis-1,2-dicarboximide in 100 ml of dimethylformamide with vigorous stirring (exothermic reaction). The mixture was then stirred at 45° C. for 2 h and subsequently cooled and poured into ice-water. After acidification with ten percent hydrochloric acid, 100 ml of methyl t-butyl ether were added and the mixture was vigorously stirred. The pale solid was filtered off with suction, washed with a little methyl t-butyl ether and water and dried at 50° C. under reduced pressure. The crude product was purified by column chromatography (silica gel, mobile phase methylene chloride/methanol 97/3. 6.7 g (68%) of product (main polar zone) were isolated with melting point 197–199° C.

c) 6-p-Fluorophenyl-1,5-cis-3-azabicyclo[4.3.0]non-6-ene

A solution of 4.0 g (16.4 mM) of 3-p-fluorophenyl-3-cyclohexene-cis-1,2-dicarboxamide in 50 ml of tetrahydrofuran was added dropwise to 1.96 g (51 mM) of lithium aluminum hydride in 60 ml of absolute tetrahydrofuran at room temperature with vigorous stirring over the course of 45 min. The mixture was then stirred for 1.5 h and subsequently refluxed for 3 h. After cooling, ten percent sodium hydroxide solution was cautiously added dropwise while cooling in ice and stirring vigorously, and the precipitated hydroxides were filtered off with suction. The filtrate was evaporated to dryness, and the residue was partitioned between water and methyl t-butyl ether at pH=10. The organic phase was extracted with five percent hydrochloric acid, made alkaline with concentrated sodium hydroxide solution and extracted twice with methyl t-butyl ether. After drying and concentration, 1.6 g (45%) of product were isolated as a pale oil.

The following can be prepared in a similar way:
c) 6-phenyl-1-5-cis-3-azabicyclo[4.3.0]non-6-ene
L. exo-6-p-Fluorophenyl-1,5-cis-3-azabicyclo[4.3.0]nonane
a) exo-3-p-Fluorophenyl-4-cyclohexene-cis-1,2-dicarboximide 12.9 g (94 mM) of finely powdered potassium carbonate were added in portions to 15.0 g (61 mM) of endo-3-p-fluorophenyl-4-cyclohexene-cis-1,2-dicarboximide in 100 ml of dimethylformamide while stirring vigorously, and the mixture was maintained at 100° C. for 2 h. It was subsequently cooled and then poured into ice-water. After acidification with concentrated hydrochloric acid and extraction with methyl t-butyl ether, the organic phase was washed with ten percent hydrochloric acid. After drying and concentration, 18.1 g of crude product were isolated and were stirred with 50 ml of ether. 12.1 g (81%) of colorless crystals were isolated with melting point 119–121° C. The configuration of the product was proved by crystal structure analysis.

b) exo-6-p-Fluorophenyl-1,5-cis-3-azabicyclo[4.3.0]non-7-ene

A solution of 6.5 g (26 mM) of 3-p-fluorophenyl-4-cyclohexene-cis-1,2-dicarboxamide in 60 ml of tetrahydrofuran was added dropwise to 3.2 g (84 mM) of lithium aluminum hydride in 120 ml of absolute tetrahydrofuran at room temperature while stirring vigorously over the course of 45 min. The mixture was stirred for 1.5 h and then refluxed for 3 h. After cooling, ten percent sodium hydroxide solution was cautiously added dropwise while cooling in ice and stirring vigorously, and the precipitated hydroxides were filtered off with suction. The filtrate was evaporated to dryness, and the residue was partitioned between ten percent hydrochloric acid and methyl t-butyl ether. The aqueous phase was washed with methyl t-butyl ether, made alkaline with concentrated sodium hydroxide solution and extracted twice with methyl t-butyl ether. After drying and concentration, 3.6 g (64%) of product were isolated as a pale oil.

c) exo-6-p-Fluoropheny-1,5-cis-3-azabicyclo[4.3.0]nonane

Obtained by catalytic hydrogenation of exo-6-p-fluorophenyl-1,5-cis-3-azabicyclo[4.3.0]non-7-ene by the method of Example F: yield 89%.

The following can be prepared in a similar way:

d) exo-6-phenyl-1,5-cis-3-azabicyclo[4.3.0]nonane

M. exo-7-Phenyl-1,5-cis-3-azabicyclo[4.3.0]non-8-ene a) exo-4-Phenyl-5-cyclohexene-cis-1,2-dicarboximide A mixture of 15.1 g (100 mM) of 4-cyclohexene-cis-1,2-dicarboximide, 28.0 ml (250 mM) of iodobenzene, 1.8 g (8.0 mM) of palladium(II) acetate, 2.1 g (8.0 mM) of triphenylphosphine, 8.5 g (100 mM) of piperidine and 4.6 g (100 mM) of formic acid in 200 ml of dimethylformamide was heated at 80° C. with vigorous stirring for 6 h. The mixture was concentrated under oil pump vacuum and then the residue was partitioned between water and methylene chloride, the mixture was acidified with ten percent hydrochloric acid, and the organic phase was dried with sodium sulfate and concentrated. The crude product (31 g) was purified by column chromatography (silica gel, mobile phase ethyl acetate/n-hexane 1/1). Two main fractions were isolated: the polar zone yielded 3.9 g (17%) of product as a yellowish oil.

b) exo-7-Phenyl-1,5-cis-3-azabicyclo[4.3.0]non-8-ene 1.0 g (26 mM) of lithium aluminum hydride was added in portions to 3.0 g (17.2 mM) of exo-4-phenyl-5-cyclohexene-cis-1,2-dicarboxamide in 150 ml of tetrahydrofuran at room temperature while stirring vigorously. The mixture was stirred for 0.5 h and then refluxed for 3 h. After cooling, ten percent sodium hydroxide solution was cautiously added dropwise while cooling in ice and stirring vigorously, and the precipitated hydroxides were filtered off with suction and washed with tetrahydrofuran. The filtrate was evaporated to dryness, and the residue was partitioned between water and methyl t-butyl ether at pH=10. After drying and concentration, 3.2 g of crude product were isolated as a dark oil. The crude product was purified by column chromatography (silica gel, mobile phase methylene chloride/methanol 1/1). 1.1 g (32%) of product were isolated as a pale oil.

N. 7-Phenyl-3-azabicyclo[4.3.0]non-1-ene a) 4-Phenyl-1-cyclohexene-1,2-dicarboximide The non-polar main fraction from the column chromatography of Example M.a) yielded 3.2 g (15%) of product as a colorless oil/crystal mixture.

b) 7-Phenyl-3-azabicyclo[4.3.0]non-1-ene

Reduction with lithium aluminum hydride as in Example M.b) yielded 0.7 g (25%) of product as a pale oil.

O. exo-7-p-Fluorophenyl-1,5-cis-3-azabicyclo[4.3.0]nonane a) 4-p-Fluorophenyl-1-cyclohexene-1,2-dicarboximide A mixture of 45.3 g (300 mM) of 4-cyclohexene-cis-1,2-dicarboximide, 82.5 ml (750 mM) of p-bromofluorobenzene, 5.4 g (24 mM) of palladium(II) acetate, 6.3 g (24 mM) of triphenylphosphine, 29.7 ml (300 mM) of piperidine and 11.4 ml (300 mM) of formic acid in 600 ml of dimethylformamide was heated at 95–100° C. with vigorous stirring for 6 h. The mixture was concentrated under oil pump vacuum, and the residue was partitioned between water and methylene chloride, the mixture was acidified with ten percent hydrochloric acid, the organic phase was washed with ten percent hydrochloric acid, dried with sodium sulfate and concentrated. The crude product (71 g) was stirred in 350 ml of ethyl acetate, with the brown solid was filtered off with suction and washed with ethyl acetate. Concentration of the filtrate afforded 56 g of crude product which was purified by column chromatography (silica gel, mobile phase ethyl acetate/n-hexane 40/60). Two main fractions were isolated: the non-polar zone yielded 13.3 g of product which was stirred with a 1:1 mixture of ethyl acetate and n-hexane. 8.9 g (12%) of product were isolated with melting point 136–137° C.

b) 7-p-Fluorophenyl-3-azabicyclo[4.3.0]non-1-ene 4.5 g (118 mM) of lithium aluminum hydride were added in portions to 9.4 g (38 mM) of 4-p-fluorophenyl-1-cyclohexene-1,2-dicarboximide in 300 ml of tetrahydrofuran at room temperature while stirring vigorously over the course of 45 min. The mixture was stirred for 0.5 h and refluxed for 6 h. After cooling, ten percent sodium hydroxide solution was cautiously added dropwise while cooling in ice and stirring vigorously, and the precipitated hydroxides were filtered off with suction and washed with tetrahydrofuran. The filtrate was evaporated to dryness, and the residue was partitioned between water and methyl t-butyl ether at pH=10. The organic phase was subsequently extracted twice with ten percent hydrochloric acid, after which the acidic aqueous phase was made alkaline again with concentrated sodium hydroxide solution. It was then extracted twice with methyl t-butyl ether. After drying and concentration, 1.8 g (22%) of product were isolated as a pale oil.

c) exo-4-p-Fluorophenyl-5-cyclohexene-cis-1,2-dicarboximide

The polar main fraction from the column chromatography of Example O.a) yielded 9.2 g of product which was digested in a little ether. 4.3 g (6%) of product were isolated with melting point 139–142° C.

d) exo-7-p-Fluorophenyl-1,5-cis-3-azabicyclo[4.3.0non-8-ene

Reduction with lithium aluminum hydride as in Example O.b) yielded 2.4 g (63%) of product as a pale oil.

e) exo-7-p-Fluorophenyl-1,5-cis-3-azabicyclo[4.3.0]nonane

Catalytic hydrogenation as in Example F yielded 2.2 g (92%) of product as a yellowish oil.

P. 6-Phenyl-1,5-cis-8-oxa-3,7-diazabicyclo[3.3.0]oct-6-ene 6.8 g (41 mM) of 1-trifluoroacetyl-3-pyrroline were added to 5.0 g (41 mM) of benzaldehyde oxime in 50 ml of methylene chloride. Then, while stirring vigorously, 36.9 g (74 mM) of a five percent strength sodium hypochlorite solution were added dropwise (exothermic reaction). The mixture was stirred for 2 h and then poured onto ice-water, made alkaline with concentrated ammonia solution and extracted twice with methylene chloride. The combined organic phases were washed with water, dried with sodium sulfate and concentrated. The crude product (13.1 g) was purified by column chromatography (silica gel, mobile phase methylene chloride). 3.5 g (30%) of the trifluoroacetyl derivative were isolated and then hydrolyzed in 2N methanolic sodium hydroxide solution at room temperature for 30 min to give the final product of melting point 78–80° C.

Reduction with sodium cyanoborohydride provided exo/endo-6-phenyl-1,5-cis-8-oxa-3,7-diazabicyclo[3.3.0]octane as a pale oil.

The following can be prepared in a similar way:
p-fluorophenyl-1,5-cis-8-oxa-3,7-diazabicyclo[3.3.0]oct-6-ene
exo/endo-6-p-fluorophenyl-1,5-cis-8-oxa-3,7-diazabicyclo[3.3.0]octane

EXAMPLE 1

3-β-[exo-6-Phenyl-7-methyl-1,5-cis-3,7-diazabicyclo[3.3.0]octan-3-yl]ethyl-2,4(1H,3H)-quinazolinedione 3.95 g (14.9 mM) of 3-β-bromoethyl-2,4(1H,3H)-quinazolinedione plus 2.0 g (14.9 mM) of finely powdered potassium carbonate and 0.5 g of potassium iodide were added to 2.5 g (12.4 mM) of exo-6-phenyl-7-methyl-1,5-cis-3,7-diazabicyclo[3.3.0]octane in 50 ml of xylene, and the mixture was refluxed for 6 h.

After cooling and concentration in a rotary evaporator, the residue was partitioned between methylene chloride and water.

The aqueous phase was back-extracted twice with methylene chloride and then the organic phase was dried with sodium sulfate and concentrated. The crude product (7.1 g) was purified by column chromatography (silica gel, mobile phase methylene chloride/methanol 95/5) to yield 2.5 g (52%) of product of melting point 128–130° C.

The following can be prepared in a similar way:
2. 3-β-[endo-6-phenyl-7-methyl-1,5-cis-3,7-diazabicyclo[3.3.0]octan-3-yl]ethyl-2,4(1H,3H)-quinazolinedione, melting point 211–213° C.,
3. 3-β-[exo-6-p-fluorophenyl-7-methyl-1,5-cis-3,7-diazabicyclo[3.3.0]octan-3-yl]ethyl-2,4(1H,3H)-quinazolinedione, decomposition point 230° C. (dihydrochloride),
4. 3-β-[exo-6-p-trifluoromethylphenyl-7-methyl-1,5-cis-3,7-diazabicyclo[3.3.0]octan-3-yl]ethyl-6-fluoro-2,4(1H,3H)-quinazolinedione,
5. 3-β-[exo-6-m-chlorophenyl-7-methyl-1,5-cis-3,7-diazabicyclo[3.3.0]octan-3-yl]ethyl-2,4(1H,3H)-quinazolinedione,
6. 3-β-[exo-6-p-methoxyphenyl-7-methyl-1,5-cis-3,7-diazabicyclo[3.3.0]octan-3-yl]ethyl-6-methyl-2,4(1H,3H)-quinazolinedione,

EXAMPLE 7

5-β-[exo-6-Phenyl-7-methyl-1,5-cis-3,7-diazabicyclo[3.3.0]octan-3-yl]ethyl-2-methylamino-3,6-dimethyl-4(3H)-pyrimidinone 3.2 g (14.9 mM) of 5-β-chloroethyl-2-methylamino-3,6-dimethyl-4(3H)-pyrimidinone plus 2.0 g (14.9 mM) of finely powdered potassium carbonate and 0.5 g of potassium iodide were added to 2.5 g (12.4 mM) of exo-6-phenyl-7-methyl-1,5-cis-3,7-diazabicyclo[3.3.0]octane in 50 ml of xylene, and the mixture was refluxed for 5 h.

After cooling and concentration in a rotary evaporator, the residue was partitioned between methylene chloride and water.

The aqueous phase was back-extracted twice with methylene chloride and then the organic phase was dried with sodium sulfate and concentrated. The crude product (5.4 g) was purified by column chromatography (silica gel, mobile phase methylene chloride/methanol 93/7) to yield 1.6 g (36%) of product of melting point decomposition above 67° C.

The following can be prepared in a similar way:

8. 5-β-[exo-6-p-Fluorophenyl-7-methyl-1,5-cis-3,7-diazabicyclo[3.3.0]octan-3-yl]ethyl-2-methylamino-3,6-dimethyl-4(3H)-pyrimidinone,
9. 1-β-[exo-6-p-Fluorophenyl-7-methyl-1,5-cis-3,7-diazabicyclo[3.3.0]octan-3-yl]ethyl-2(3H)-benzimidazolone,
10. 5-β-[exo-6-p-Nitrophenyl-7-methyl-1,5-cis-3,7-diazabicyclo[3.3.0]octan-3-yl]ethyl-2-methylamino-3,6-dimethyl-4(3H)-pyrimidinone,
11. 5-β-[exo-6-Phenyl-7-methyl-1,5-cis-3,7-diazabicyclo[3.3.0]octan-3-yl]ethyl-2-methylamino-3,6-dimethyl-4(3H)-pyrimidinone,
12. 5-β-[endo-6-Phenyl-7-methyl-1,5-cis-3,7-diazabicyclo[3.3.0]octan-3-yl]ethyl-2-methylamino-3,6-dimethyl-4(3H)-pyrimidinone,
13. 3-β-[exo-6-p-Fluorophenyl-7-methyl-1,5-cis-3,7-diazabicyclo[3.3.0]octan-3-yl]ethyl-2-methyl-4H-pyrido[1.2-a]pyrimidin-4-one,
14. 1-β-[exo-6-p-Fluorophenyl-7-methyl-1,5-cis-3,7-diazabicyclo[3.3.0]octan-3-yl]ethyl-2-indolinone,
15. 6-β-[exo-6-p-Fluorophenyl-7-methyl-1,5-cis-3,7-diazabicyclo[3.3.0]octan-3-yl]ethyl-7-methyl-5H-thiazolo[3.2-a]pyrimidin-5-one,
16. 1-β-[exo-6-p-Fluorophenyl-7-methyl-1,5-cis-3,7-diazabicyclo[3.3.0]octan-3-yl]ethyl-2(1H)-quinolone,
17. 3-β-[7-Phenyl-1,5-cis-3,7-diazabicyclo[3.3.0]octan-3-yl]-ethyl-2,4-(1H,3H)-quinazolinedione, melting point 215–216° C.,
18. 3-β-[7-p-Fluorophenyl-1,5-cis-3,7-diazabicyclo[3.3.0]-octan-3-yl]-ethyl-2,4(1H,3H)-quinazolinedione,
19. 5-β-[7-p-Fluorophenyl-1,5-cis-3,7-diazabicyclo[3.3.0]octan-3-yl]-ethyl-2-methylamino-3,6-dimethyl-4(3H)-pyrimidinone,
20. 3-β-[exo-6-p-Fluorophenyl-3-azabicyclo[3.1.0]hexan-3-yl]-ethyl-2,4(1H,3H)-quinazolinedione,
21. 3-β-[exo-6-p-Phenyl-3-azabicyclo[3.1.0]hexan-3-yl]ethyl-2,4-(1H,3H)-quinazolinedione,
22. 3-β-[6,6-Diphenyl-3-azabicyclo[3.1.0]hexan-3-yl]ethyl-2,4(1H,3H)-quinazolinedione,
23. 5-β-[exo-6-p-Fluorophenyl-3-azabicyclo[3.1.0]hexan-3-yl]ethyl-2-methylamino-3,6-dimethyl-4(3H)-pyrimidinone,
24. 6-β-[exo-6-m-Chlorophenyl-3-azabicyclo[3.1.0]hexan-3-yl]ethyl-7-methyl-5H-thiazolo[3,2-a]pyrimidin-5-one,
25. 3-β-[6-p-Fluorophenyl-1,5-cis-3-azabicyclo[3.3.0]oct-6-en-3-yl]ethyl-2,4(1H,3H)-quinazolinedione, melting point 265–267° C.,
26. 5-β-[6-p-Fluorophenyl-1,5-cis-3-azabicyclo[3.3.0]oct-6-en-3-yl]ethyl-2-methylamino-3,6-dimethyl-4(3H)-pyrimidinone,
27. 6-β-[6-p-Fluorophenyl-1,5-cis-3-azabicyclo[3.3.0]oct-6-en-3-yl]-ethyl-7-methyl-5H-thiazolo[3,2-a]pyrimidin-5-one,
28. 1-β-[6-Phenyl-1,5-cis-3-azabicyclo[3.3.0]oct-6-en-3-yl]-ethyl-2(3H)-benzimidazolone,
29. 1-β-[6-p-Fluorophenyl-1,5-cis-3-azabicyclo[3.3.0]oct-6-en-3-yl]-ethyl-2-indolinone,
30. 1-β-[6-p-Fluorophenyl-1,5-cis-3-azabicyclo[3.3.0]oct-6-en-3-yl]-ethyl-2(1H)-quinolone,
31. 3-β-[exo-6-p-Fluorophenyl-1,5-cis-3-azabicyclo[3.3.0]octan-3-yl]ethyl-2,4-(1H,3H)-quinazolinedione, melting point 129–130° C.,
32. 5-β-[exo-6-p-Fluorophenyl-1,5-cis-3-azabicyclo[3.3.0]octan-3-yl]ethyl-2-methylamino-3,6-dimethyl-4(3H)-pyrimidinone,
33. 6-β-[exo-6-Phenyl-1,5-cis-3-azabicyclo[3.3.0]octan-3-yl]ethyl-7-methyl-5H-thiazolo[3.2-a]pyrimidin-5-one, 34. 1-β-[exo-6-p-Fluorophenyl-1,5-cis-3-azabicyclo(3.3.0]
octan-3-yl]ethyl-2-indolinone,
35. 1-β-[exo-6-p-Fluorophenyl-1,5-cis-3-azabicyclo[3.3.0]
octan-3-yl]ethyl-2(1H)-quinolone,
36. 3-β-[endo-6-p-Fluorophenyl-1,5-cis-3-azabicyclo[3.3.0]
octan-3-yl]ethyl-2,4-(1H,3H)-quinazolinedione, melting point 182–183° C.,
37. 5-β-[endo-6-p-Fluorophenyl-1,5-cis-3-azabicyclo[3.3.0]
octan-3-yl]ethyl-2-methylamino-3,6-dimethyl-4(3H)
pyrimidinone,
38. 6-β-[endo-Phenyl-1,5-cis-3-azabicyclo[3.3.0]octan-3-yl]ethyl-7-methyl-5H-thiazolo[3.2-a]pyrimidin-5-one,
39. 1-β-[endo-6-p-Fluorophenyl-1,5-cis-3-azabicyclo[3.3.0]
octan-3-yl]ethyl-2-indolinone,
40. 1-β-[endo-6-p-Fluorophenyl-1,5-cis-3-azabicyclo[3.3.0]
octan-3-yl]ethyl-2(1H)-quinolone,
41. 3-β-[exo-7-p-Fluorophenyl-1,5-cis-3-azabicyclo[3.3.0]
octan-3-yl]ethyl-2,4(1H,3H)-quinazolinedione,
42. 5-β-[exo-7-p-Fluorophenyl-1,5-cis-3-azabicyclo[3.3.0]
octan-3-yl]ethyl-2-methylamino-3,6-dimethyl-4(3H)-pyrimidinone,
43. 6-β-[exo-7-Phenyl-1,5-cis-3-azabicyclo[3.3.0]octan-3-yl]ethyl-7-methyl-5H-thiazolo[3.2-a]pyrimidin-5-one,
44. 1-β-[exo-7-p-Fluorophenyl-1,5-cis-3-azabicyclo[3.3.0]
octan-3-yl]ethyl-2-indolinone,
45. 1-β-[exo-7-p-Fluorophenyl-1,5-cis-3-azabicyclo[3.3.0]
octan-3-yl]ethyl-2(1H)-quinolone,
46. 3-β-[endo-6-p-Fluorophenyl-1,5-cis-3-azabicyclo[4.3.0]
non-3-yl]-ethyl-2,4-(1H,3H)-quinazolinedione, melting point 200–202° C.,
47. 5-β-[endo-6-p-Fluorophenyl-1,5-cis-3-azabicyclo[4.3.0]
non-3-yl]ethyl-2-methylamino-3,6-dimethyl-4(3H)-pyrimidinone, melting point 68–70° C.,
48. 3-β-[endo-6-Phenyl-1,5-cis-3-azabicyclo[4.3.0]non-3-yl]ethyl-2,4-(1H,3H)-quinazolinedione, melting point 100–101° C.,
49. 5-β-[endo-6-Phenyl-1,5-cis-3-azabicyclo[4.3.0]non-3-yl]ethyl-2-methylamino-3,6-dimethyl-4(3H)-pyrimidinone, melting point 182–184° C. (dihydrochloride).
50. 3-β-[endo-6-p-Trifluoromethylphenyl-1,5-cis-3-azabicyclo[4.3.0]non-3-yl]ethyl-2,4-(1H,3H)-quinazolinedione,
51. 5-β-[endo-6-p-Trifluoromethylphenyl-1,5-cis-3-azabicyclo[4.3.0]non-3-yl]ethyl-2-methylamino-3,6-dimethyl-4(3H)-pyrimidinone,
52. 3-β-[endo-6-p-Fluorophenyl-1,5-cis-3-azabicyclo[4.3.0]
non-7-en-3-yl]ethyl-2,4-(1H,3H)-quinazolinedione, melting point 174–176° C.
53. 5-β-[endo-6-p-Fluorophenyl-1,5-cis-3-azabicyclo[4.3.0]
non-7-en-3-yl]ethyl-2-methylamino-3,6-dimethyl-4(3H)-pyrimidinone,
54. 1-β-[endo-6-p-Fluorophenyl-1,5-cis-3-azabicyclo[4.3.0]
non-7-en-3-yl]ethyl-2(3H)-benzimidazolone,
55. 1-β-[endo-6-p-Fluorophenyl-1,5-cis-3-azabicyclo[4.3.0]
non-7-en-3-yl]ethyl-2-indolinone,
56. 3-β-[6-p-Fluorophenyl-1,5-cis-3-azabicyclo[4.3.0]non-6-en-3-yl]ethyl-2,4-(1H,3H)-quinazolinedione, melting point 237–239° C. (fumarate),
57. 5-β-[6-p-Fluorophenyl-1,5-cis-3-azabicyclo[4.3.0]non-6-en-3-yl]ethyl-2-methylamino-3,6-dimethyl-4(3H)-pyrimidinone, melting point 189–192° C. (dihydrochloride),
58. 3-β-[6-Phenyl-1,5-cis-3-azabicyclo[4.3.0]non-6-en-3-yl]ethyl-2,4-(1H,3H)quinazolinedione,
59. 5-β-[6-Phenyl-1,5-cis-3-azabicyclo[4.3.0]non-6-en-3-yl]ethyl-2-methylamino-3,6-dimethyl-4(3H)-pyrimidinone,
60. 3-β-[6-p-Trifluoromethylphenyl-1,5-cis-3-azabicyclo[4.3.0]non-6-en-3-yl]ethyl-2,4-(1H,3H)-quinazolinedione,
61. 5-β-[6-p-Trifluoromethylphenyl-1,5-cis-3-azabicyclo[4.3.0]non-6-en-3-yl]ethyl-2-methylamino-3,6-dimethyl-4(3H)-pyrimidinone,
62. 1-β-[6-p-Fluorophenyl-1,5-cis-3-azabicyclo[4.3.0]non-6-en-3-yl]ethyl-2(3H)-benzimidazolone,
63. 1-β-[6-p-Fluorophenyl-1,5-cis-3-azabicyclo[4.3.0]non-6-en-3-yl]ethyl-2-indolinone,
64. 1-β-[6-p-Fluorophenyl-1,5-cis-3-azabicyclo[4.3.0]non-6-en-3-yl]-ethyl-2(1H)-quinolone,
65. 3-β-[exo-6-p-Fluorophenyl-1,5-cis-3-azabicyclo[4.3.0]
non-7-en-3-yl]ethyl-2,4-(1H,3H)-quinazolidone, melting point 142–143° C. (fumarate),
66. 5-β-[exo-6-p-Fluorophenyl-1,5-cis-3-azabicyclo[4.3.0]
non-7-en-3-yl]ethyl-2-methylamino-3,6-dimethyl-4(3H)-pyrimidinone, melting point 63–65° C.,
67. 3-β-[exo-6-p-Fluorophenyl-1,5-cis-3-azabicyclo[4.3.0]
non-7-en-3-yl]ethyl-2-methyl-4H-pyrido[1.2-a]pyrimidin-4-one,
68. 1-β-[exo-6-p-Fluorophenyl-1,5-cis-3-azabicyclo[4.3.0]
non-7-en-3-yl]ethyl-2(1H)-quinolone,
69. 1-β-[exo-6-p-Fluorophenyl-1,5-cis-3-azabicyclo[4.3.0]
non-7-en-3-yl]ethyl-2(3H)-benzimidazolone,
70. 1-β-[exo-6-p-Fluorophenyl-1,5-cis-3-azabicyclo[4.3.0]
non-7-en-3-yl]ethyl-2-indolinone,
71. 3-β-[exo-6-Phenyl-1,5-cis-3-azabicyclo[4.3.0]non-7-en-3-yl]ethyl-2,4-(1H,3H)-quinazolinedione,
72. 5-β-[exo-6-Phenyl-1,5-cis-3-azabicyclo[4.3.0]non-7-en-3-yl]ethyl-2-methylamino-3,6-dimethyl-4(3H)-pyrimidinone,
73. 3-β-[exo-6-p-Fluorophenyl-1,5-cis-3-azabicyclo[4.3.0]
non-3-yl]-ethyl-2,4-(1H,3H)-quinazolinedione, melting point 103–105° C.,
74. 5-β-[exo-6-p-Fluorophenyl-1,5-cis-3-azabicyclo[4.3.0]
non-3-yl]-ethyl-2-methylamino-3,6-dimethyl-4(3H)-pyrimidinone, melting point 68–70° C.,
75. 3-β-[exo-6-Phenyl-1,5-cis-3-azabicyclo[4.3.0]non-3-yl]
ethyl-2,4-(1H,3H)-quinazolinedione,
76. 5-β-[exo-6-Phenyl-1,5-cis-3-azabicyclo[4.3.0]non-3-yl]
ethyl-2-methylamino-3,6-dimethyl-4(3H)-pyrimidinone,
77. 6-β-[exo-6-p-Fluorophenyl-1,5-cis-3-azabicyclo[4.3.0]
non-3-yl]ethyl-7-methyl-5H-thiazolo[3.2-a]pyrimidin-5-one,
78. 1-β-[exo-6-p-Fluorophenyl-1,5-cis-3-azabicyclo[4.3.0]
non-3-yl]ethyl-2(3H)-benzimidazolone,
79. 1-β-[exo-6-p-Fluorophenyl-1,5-cis-3-azabicyclo[4.3.0]
non-3-yl]-ethyl-2-indolinone,
80. 1-β-[exo-6-p-Fluorophenyl-1,5-cis-3-azabicyclo[4.3.0]
non-3-yl]ethyl-2(1H)-quinolone,
81. 3-β-[exo-7-Phenyl-1,5-cis-3-azabicyclo[4.3.0]non-8-en-3-yl]ethyl-2,4-(1H,3H)-quinazolinedione,
82. 5-β-[exo-7-Phenyl-1,5-cis-3-azabicyclo[4.3.0]non-8-en-3-yl]ethyl-2-methylamino-3,6-dimethyl-4(3H)-pyrimidinone, melting point 75–77° C. (dihydrochloride x H₂O),
83. 3-β-[exo-7-p-Fluorophenyl-1,5-cis-3-azabicyclo[4.3.0]
non-8-en-3-yl]ethyl-2,4-(1H,3H)-quinazolinedione, melting point 159–162° C. (fumarate),
84. 5-β-[exo-7-p-Fluorophenyl-1,5-cis-3-azabicyclo[4.3.0]
non-8-en-3-yl]-ethyl-2-methylamino-3,6-dimethyl-4(3H)-pyrimidinone, melting point 240–243° C. (dihydrochloride),
85. 3-β-[7-p-Fluorophenyl-3-azabicyclo[4.3.0]non-1-en-3-yl]ethyl-2,4-(1H,3H)-quinazolinedione, melting point 75–77° C., 86. 5-β-[7-Phenyl-3-azabicyclo[4.3.0]non-1-en-3-yl]ethyl-2-methylamino-3,6-dimethyl-4(3H)-pyrimidinone, melting point 155–157° C. (dihydrochloride x 2H₂O),
87. 5-β-[7-p-Fluorophenyl-3-azabicyclo[4.3.0]non-1-en-3-yl]-ethyl-2-methylamino-3,6-dimethyl-4(3H)-pyrimidinone, melting point 175–177° C. (dihydrochloride),
88. 3-β-[exo-7-p-Fluorophenyl-1,5-cis-3-azabicyclo[4.3.0]non-3-yl]-ethyl-2,4-(1H,3H)-quinazolinedione,
89. 5-β-[exo-7-p-Fluorophenyl-1,5-cis-3-azabicyclo[4.3.0]non-3-yl]-ethyl-2-methylamino-3,6-dimethyl-4(3H)-pyrimidinone,
90. 1-β-[exo-7-p-Fluorophenyl-1,5-cis-3-azabicyclo[4.3.0]non-3-yl]-ethyl-2(3H)-benzimidazolone,
91. 1-β-[exo-7-p-Fluorophenyl-1,5-cis-3-azabicyclo[4.3.0]non-3-yl]-ethyl-2-indolinone,
92. 1-p-[exo-7-p-Fluorophenyl-1,5-cis-3-azabicyclo[4.3.0]non-3-yl]ethyl-2(1H)-quinolone,
93. 3-β-[6-p-Fluorophenyl-1,5-cis-8-oxa-3,7-diazabicyclo[3.3.0]-oct-6-en-3-yl]ethyl-2,4-(1H,3H)-quinazolinedione, melting point 90–92° C.,
94. 5-β-[6-p-Fluorophenyl-1,5-cis-8-oxa-3,7-diazabicyclo[3.3.0]-oct-6-en-3-yl]ethyl-2-methylamino-3,6-dimethyl-4(3H)-pyrimidinone, melting point 231–233° C.,
95. 3-β-[exo/endo-6-p-Fluorophenyl-1,5-cis-8-oxa-3,7-diazabicyclo[3.3.0]octan-3-yl]ethyl-2,4-(1H,3H)-quinazolinedione,
96. 5-β-[exo/endo-6-p-Fluorophenyl-1,5-cis-8-oxa-3,7-diazabicyclo[3.3.0]octan-3-yl]ethyl-2-methylamino-3,6-dimethyl-4(3H)-pyrimidinone,
97. 1-β-[6-p-Fluorophenyl-1,5-cis-8-oxa-3,7-diazabicyclo[3.3.0]-oct-6-en-3-yl]ethyl-2-indolinone,
98. 6-β-[6-Phenyl-1,5-cis-8-oxa-3,7-diazabicyclo[3.3.0]oct-6-en-3-yl]ethyl-7-methyl-5H-thiazolo[3,2-a]pyrimidin-5-one.

We claim:
1. An N-substituted 3-azabicycloalkane of the formula I

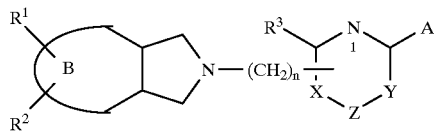

(I)

wherein
B is a 3-, 5- or 6-membered ring which, in addition to carbon atoms, may contain 1 nitrogen atom and/or 1 oxygen atom and optionally a double bond,
$R^1$ is phenyl which is unsubstituted or mono- or disubstituted by halogen atoms, $C_1$–$C_4$-alkyl, trifluoromethyl, hydroxyl, $C_1$–$C_4$-alkoxy, amino, monomethylamino, dimethylamino, cyano or nitro groups,
$R^2$ is hydrogen, $C_1$–$C_4$-alkyl, or phenyl which is unsubstituted or substituted by halogen, methoxy, hydroxyl or amino,
n is 0, 1, 2, 3, or 4,
$R^3$ is hydrogen, hydroxyl, $C_1$–$C_4$-alkyl or $C_1$–$C_4$-alkoxy or,
is together with the adjacent carbon atom, a C=O or C=S group,
one of X and Y is a carbon atom, CH or $CH_2$, and the other is a NH or $C_1$–$C_4$-alkyl-N group or a nitrogen atom,
Z is a C=O group, C=S group or is a CH or $CH_2$ group in which one hydrogen atom can be replaced by a hydroxyl, amino or $C_1$–$C_4$-alkoxy group or a halogen atom, and
A is $C_1$–$C_4$-alkylamino, or
is a $C_3$–$C_4$-alkylene group which is linked to Y and which may contain one or two non-cumulative double bonds and where the ring may be monosubstituted either by a fluorine or chlorine atom or a methyl, methoxy, nitro or amino group or, in the case of a benzene ring, the latter may be mono-, di- or trisubstituted by fluorine or chlorine atoms or methyl, trifluoromethyl, nitro, hydroxyl, methoxy, amino, monomethyl- or dimethylamino groups,
and where the ring on the right of the formula I may have on nitrogen atom No. 1 a hydrogen atom or a $C_1$–$C_4$-alkyl group and may contain 1, 2 or 3 non-cumulative double bonds,
or salts thereof with physiologically tolerated acids.
2. An N-substituted 3-azabicycloalkane of the formula I as defined in claim 1, wherein $R^1$ is phenyl which is unsubstituted or mono- or disubstituted by fluorine, chlorine, methoxy, nitro, trifluoromethyl, hydroxyl or amino, or salts thereof with physiologically tolerated acids.
3. An N-substituted 3-azabicycloalkane of the formula I as defined in claim 1, wherein $R^2$ is hydrogen or methyl, or salts thereof with physiologically tolerated acids.
4. An N-substituted 3-azabicycloalkane of the formula I as defined in claim 1, wherein $R^3$ is methyl or hydroxyl, or salts thereof with physiologically tolerated acids.
5. An N-substituted 3-azabicycloalkane of the formula I as defined in claim 1, wherein n is 2, or salts thereof with physiologically tolerated acids.
6. An N-substituted 3-azabicycloalkane of the formula I as defined in claim 3, wherein
B is a 3-, 5- or 6-membered ring which may contain a double bond,
$R^1$ is phenyl which is unsubstituted or mono- or disubstituted by halogen atoms, $C_1$–$C_4$-alkyl, trifluoromethyl, cyano or nitro groups,
$R^2$ is hydrogen,
n is 2, 3, or 4,
Z is a C=O group, or a CH or $CH_2$ group, and
A is $C_1$–$C_4$-alkylamino, or
is a $C_3$–$C_4$-akylene group which is linked to Y and which may contain one or two non-cumulative double bonds and in the case of a benzene ring, the latter may be mono-, di- or trisubstituted by fluorine or chlorine atoms or methyl, trifluoromethyl, nitro, hydroxyl or methoxy groups,
or salts thereof with physiologically tolerated acids.
7. An N-substituted 3-azabicycloalkane of the formula I as defined in claim 1, wherein
one of X and Y is a carbon atom, CH or $CH_2$, and the other is a NH or $C_1$–$C_4$-alkyl-N group or a nitrogen atom,
Z is a C=O group, C=S group or
is a CH or $CH_2$ group in which one hydrogen atom can be replaced by a hydroxyl, amino or $C_1$–$C_4$-alkoxy group or a halogen atom, and
A is $C_1$–$C_4$-alkylamino, or
is a $C_3$–$C_4$-akylene group which is linked to Y and which may contain one or two non-cumulative double bonds and where the ring may be monosubstituted either by a fluorine or chlorine atom or a methyl, methoxy, nitro or amino group or, in the case of a benzene ring, the latter may be mono-, di- or trisubstituted by fluorine or chlorine atoms or methyl, trifluoromethyl, nitro, hydroxyl, methoxy, amino, monomethyl- or dimethylamino groups, or salts thereof with physiologically tolerated acids.

8. An N-substituted 3-azabicycloalkane of the formula I as defined in claim 1, wherein one of X and Y is a carbon atom, CH or $CH_2$, and the other is a NH or $C_1$–$C_4$-alkyl-N group or a nitrogen atom, Z is a C=O group, C=S group or is a CH or $CH_2$ group in which one hydrogen atom can be replaced by a hydroxyl, amino or $C_1$–$C_4$-alkoxy group or a halogen atom, and A is $C_1$–$C_4$-alkylamino, or is a $C_3$–$C_4$-akylene group which is linked to Y and which may contain one or two non-cumulative double bonds and where the ring may be monosubstituted either by a fluorine or chlorine atom or a methyl, methoxy, nitro or amino group or, in the case of a benzene ring, the latter may be mono-, di- or trisubstituted by fluorine or chlorine atoms or methyl, trifluoromethyl, nitro, hydroxyl, methoxy, amino, monomethyl- or dimethylamino groups, or salts thereof with physiologically tolerated acids.

9. A therapeutic composition comprising an N-substituted 3-azabicycloalkane of the formula I as defined in claim 1 or its pharmacologically suitable acid addition salt and conventional excipients and diluents.

* * * * *